United States Patent [19]

Helmlinger

[11] Patent Number: 5,292,902

[45] Date of Patent: Mar. 8, 1994

[54] PROCESS FOR THE MANUFACTURE OF ODORANTS AND INTERMEDIATES USED THEREIN

[75] Inventor: Daniel Helmlinger, Dübendorf, Switzerland

[73] Assignee: Givaudan-Roure Corporation, Clifton, N.J.

[21] Appl. No.: 919,520

[22] Filed: Jul. 24, 1992

[30] Foreign Application Priority Data

Aug. 2, 1991 [CH] Switzerland .................. 2308/91

[51] Int. Cl.$^5$ .................. C07D 307/92; C07C 255/07
[52] U.S. Cl. .................. 549/458; 558/430
[58] Field of Search .................. 549/458; 558/430

[56] References Cited

U.S. PATENT DOCUMENTS 2,809,996 10/1957 Stoll .
4,814,469 3/1989 Whitesides et al. .................. 549/458
5,077,417 12/1991 Schutte-Elte et al. .................. 549/458

FOREIGN PATENT DOCUMENTS 0165458 12/1985 European Pat. Off. .
0170955 2/1986 European Pat. Off. .
   13535 7/1957 Fed. Rep. of Germany .
3240054 5/1984 Fed. Rep. of Germany .
9012793 11/1990 Fed. Rep. of Germany .
0013778 1/1985 Japan .
0064975 4/1985 Japan .
  123483 7/1985 Japan .
2083378 3/1990 Japan .

OTHER PUBLICATIONS

R. Reeves, "Chemistry of the Carbonyl Group", S. Patai, editor, Interscience, N.Y., 1966, p. 593 ff.
L. Rand, J. Org. Chem. 27 (1962) p. 3505 ff.
J. H. Clark, Chem. Rev. 80 (1980) p. 429 ff.
Organikum, 17th Edition, VEB Deutscher Verlag der Wissenschaften, Berlin, 1988, p. 424 ff.
G. Lucius, Archiv der Pharmazie, 291 (63) (1958), p. 58 ff.
G. Lucius, Chem. Ber. 93 (1960), p. 2663 ff.
G. Lucius, Angew. Chem., 68, (1956) p. 247.
A. Saito et al., Chem. Lett. (1981) p. 757 ff.
A. Saito et al., ibid., (1983) p. 729 ff.
T. Kawanobe et al., Agric. Biol. Chem. 50 (6) (1985) p. 1475 ff.
Chemical Abstract 94:15913q for V. E. Sibirtseva et al., Maslo–Zhir. Prom-st. 1980 (7) 29–30.
Chemical Abstract 93:114751W for ibid., 1979 (12) 25–26.
Derwent Abstract 13671A/07 for USSR Patent 559,916; Jun. 1977.
M. Stoll et al., Helv. Chim. Acta 33 (1950) 1251 ff.
Chemical Abstract 78:111554p and Derwent Abstract 11939U-DE for USSR Patent 345,153; Jul. 1972.
R. Cambie et al., Aust. J. Chem. 24 (1971) p. 583 ff. and Chemical Abstract 74:76550C.
Derwent Abstract 86–085735/13 for Japanese Patent Publication J6 1033–184; Feb. 1986.
P. Vlad et al., Synthesis (1983) p. 216 ff.

*Primary Examiner*—C. Warren Ivy
*Assistant Examiner*—A. A. Owens
*Attorney, Agent, or Firm*—George M. Gould; George W. Johnston

[57] ABSTRACT

The invention concerns a process for the manufacture of a mixture of (3aα,5aβ,9aα,9bβ)-dodecahydro-3a,6,6,9a-tetramethylnaphtho-[2,1-b]furan and (3aα,5aβ,9aα,9bα)-dodecahydro-3a,6,6,9a-tetramethylnaphtho[2,1-b]furan which utilizes the substituted hexenoic acids, 6-(2',6',6'-trimethyl-cyclohex-1'-en-1'-yl)-4-methyl-hex-2- or -3-enoic acid. The invention also concerns nitriles and a process for manufacture of the hexonic acids from the nitriles, having the formula

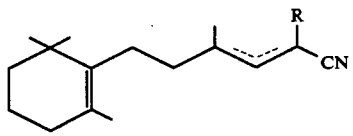

II wherein one of the bonds denotes a single bond and the other denotes a double bond, and, R represents hydrogen or the ester group COOR$^1$ in which R$^1$ represents a lower alkyl or aryl group.

5 Claims, No Drawings

PROCESS FOR THE MANUFACTURE OF ODORANTS AND INTERMEDIATES USED THEREIN

BACKGROUND OF THE INVENTION

1. Field of the Invention

The invention concerns a process for the manufacture of odorants, and novel nitriles used therein.

2. Background Art

The expensive, optically active odorant (−)-(3aR-(3aα,5aβ,9aα,9bβ))-dodecahydro-3a,6,6,9a-tetramethyl-naphtho[2,1-b]furan, is commercially available under various trade names, namely AMBROX® (Firmenich), AMBROXAN® (Henkel), AMBERLYN® (Quest), SYLVAMBER® (BASF) and AMBROXID® (Haarman & Reimer). Several processes for the manufacture of (−)-(3aR-(3aα,5aβ,9aα,9bβ))-dodecahydro-3a,6,6,9a-tetramethyl-naphtho[2,1-b]furan are known. These processes all start with sclareolid, i.e., (3aR-(3aα,5aβ,9aα,9bβ))-decahydro-3a,6,6,9a-tetramethylnaphtho[2,1-b]furan-2(1H)-one. Sclareolid itself is obtained by oxidation of sclareol (muscatel sage oil) by way of an oxidizing agent such as chromic acid. Sclareol in turn is obtained from the natural source Salvia sclarea by extraction. At present, however, the amount of commercially available sclareol is limited and the price can fluctuate enormously depending on the harvest of Salvia sclarea. A further disadvantage of this process is use of chromic acid in the oxidation step which is problematic from the point of view of environmental protection. There accordingly exists a need for an industrially realizable process for the manufacture of dodecahydro-3a,6,6,9a-tetramethylnaphtho[2,1-]furan, which does not use sclareol and, accordingly is not dependant on the availability of sclareol and, moreover, which is more economical and more environmentally friendly than the process hitherto used. This is now possible by means of the process in accordance with the invention.

SUMMARY OF THE INVENTION

The invention concerns a process for the manufacture of substituted hexenonic acids, namely 6-(2',6',6'-trimethyl-cyclohex-1'-en-1'-yl)-4-methyl-hex-2- or -3-enoic acid (I), which are suitable as intermediates for the production of odorants which consist essentially of a mixture of (±)-(3aα,5aβ,9aα,9bβ)-dodecahydro-3a,6,6,9a-tetramethylnaphtho[2,1-b]furan and (±)-(3aα,5aβ,9aα,9bα)-dodecahydro-3a,6,6,9a-tetramethylnaphtho[2,1-b]furan. These are known, inter alia, under the trade names AMBROX DL® (Firmenich), SYNAMBRAN® (Wacker), and FIXAMBRENE™ (Givaudan-Roure) and are suitable replacements for the expensive optically active (−)-[3aR-(3aα,5aβ,9aα,9bβ))-dodecahydro-3a,6,6,9a-tetramethyl-naphtho[2,1-b]furan.

The invention also concerns the process for the manufacture of the aforementioned mixture of (3aα,5aβ,9aα,9bβ)-dodecahydro-3a,6,6,9a-tetramethylnaphtho-[2,1-b]furan and (3aα,5aβ,9aα,9bα)-dodecahydro-3a,6,6,9a-tetramethylnaphtho[2,1-b]furan which utilizes the hexenoic acids.

This process comprises (a) saponifying a compound of the general formula II

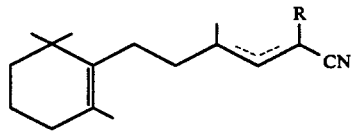

wherein one of the bonds denotes a single bond and the other denotes a double bond, and, R represents hydrogen or the ester group $COOR^1$ in which $R^1$ represents a lower alkyl or aryl group, and, where R in formula II represents the ester group $COOR^1$, decarboxylating said group, to produce a compound of the formula I

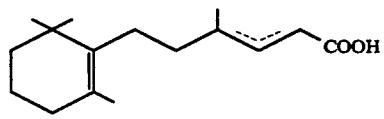

(i.e., 6-(2',6',6'-trimethyl-cyclohex-1'-en-1'-yl)-4-methyl-hex-2-enoic acid and, respectively, 6-(2',6',6'-trimethyl-cyclohex-1'-en-1'-yl)-4-methyl-hex-3-enoic acid) and, b) converting said compound of formula I in a known manner into a mixture of (3aα,5aβ,9aα,9bβ)-dodecahydro-3a,6,6,9a-tetra-methylnaphtho[2,1-b]furan and (3aα,5aβ,9aα,9bα)-dodecahydro-3a,6,6,9a-tetramethylnaphtho[2,1-b]furan.

The compounds of formula II are novel and are also a part of the present invention. These compounds can be prepared, for example, by treating 4(-2',6',6'-trimethyl-cyclohex-1'-en-1'-yl)-2-methyl-butanal, i.e. the compound of the formula

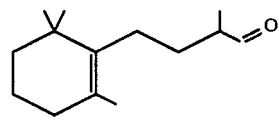

with cyanoacetic acid or a lower alkyl or aryl ester thereof, i.e. with a compound of the formula

      IV wherein $R^2$ represents hydrogen, a lower alkyl group or an aryl group. This process is a further object of the present invention.

DESCRIPTION OF THE PREFERRED EMBODIMENTS

The usual abbreviated representation of the structural formulae which are used in chemistry, especially carotinoid chemistry, are used herein. Aliphatic chains and cyclohexene rings and methyl substituents themselves are represented by single lines. In the definition of the compounds of formulas II and IV, "lower alkyl" signifies especially a straight-chain or branched alkyl residue containing 1 to 6 carbon atoms, such as, for example, methyl, ethyl, n-propyl, isopropyl, n-butyl, tert.butyl, n-pentyl, neopentyl and n-hexyl. "Aryl" signifies in the scope of the present invention especially a phenyl group which is optionally mono- or multiply-substituted with methyl, such as, for example, phenyl, o-, m- or p-tolyl and the xylyls.

Geometric isomerism occurs by virtue of the presence of the aliphatic C=C double bond in the compounds of formulas I and II, i.e, the compound I or II is present in the cis- (Z-) form or the trans- (E-) form. Moreover, the possible presence of an asymmetric carbon atom means that the compounds II can occur in optically isomeric forms. Unless otherwise indicated, formulas I and, respectively, II are intended to embrace the isomeric forms which are possible as well as mixtures of isomers.

The saponification of the compound of general formula II and, where applicable, the subsequent decarboxylation can conveniently be carried out by treating the compound of formula II in an inert protic organic solvent such as an alcohol, e.g. ethanol or isopropanol, or a glycol, e.g. mono-, di- or triethylene glycol; in an aromatic hydrocarbon, e.g. benzene, toluene or a xylene; in a cyclic ether, e.g. tetrahydrofuran or dioxan; or in water with a base at temperatures between about 20° C. and about 130° C., especially at the reflux temperature of the reaction mixture. Alkali metal hydroxides are preferably used as the base, with sodium hydroxide and potassium hydroxide being especially preferred. If R in formula II signifies an ester group, this is converted under the reaction conditions into the carboxy group which, in turn, is then decarboxylated. The reaction which may take several hours to complete, is worked-up in a manner known per se, e.g. by acidifying the mixture with sulphuric acid, extracting with a water-immiscible organic solvent such as, for example, diethyl ether, purifying the organic phase and evaporating the organic solvent. Particulars of this type of reaction are described, for example, in Organikum, 17th Edition, 1988, page 424.

The product can be obtained as a mixture of two or more isomers. When the starting material of formula II is present as a mixture of isomers, isomer mixtures are obtained. Where desired, the isomers can be separated according to methods known per se, such as fractional crystallization or column chromatography. In practice, however, this is usually not necessary, as the reaction product is converted in a multistage process into the desired odorant and the separation is carried out in the course of this conversion.

The process for the manufacture of compounds of formula II is a Knoevenagel type condensation reaction which can conveniently be carried out using an organic solvent and a small amount of a weak base or using a Lewis acid. Suitable solvents are aromatic hydrocarbons, e.g. benzene, toluene and the xylenes; alcohols, e.g. methanol and ethanol; and aliphatic or cyclic ethers, e.g. diethyl ether, tetrahydrofuran and dioxan. Examples of suitable bases are ammonia and primary, secondary and tertiary amines, especially mono-, di- and triethylamine, piperidine, pyridine, quinoline and aniline, as well as salts thereof, especially ammonium acetate and pyridinium acetate. (See, inter alia, R. L. Reeves, Chemistry of the Carbonyl Group, Editor S. Patai, (1966) Interscience Publishers, 593–600 for examples of the Knoevenagel reaction using such bases.) Where the reaction is catalyzed with a Lewis acid, potassium fluoride or potassium iodide is preferably used as the catalyst. (See, inter alia, L. Rand et al., J. Org. Chem. 1962, 3505; and J. H. Clark, Chem. Rev. 1980, 80, 429–452.) The reaction is conveniently effected at temperatures between room temperature and about 180° C., especially at room temperature or at the reflux temperature of the reaction mixture (about 70°–110° C.). The compounds of formula II can be isolated, purified and, if required, separated into the individual isomers according to methods known per se.

Especially preferred compounds of formula II are 6-(2', 6',6'-trimethyl-cyclohex-1'-en-1'-yl)-4-methyl-hex-3-enenitrile and the methyl, ethyl, isopropyl, n-butyl and tert.butyl esters of 6-(2',6',6'-trimethyl-cyclohex-1'-en-1'-yl)-4-methyl-2-cyano-hex-2-enoic acid.

The two starting materials of formulae III and IV are known compounds.

The conversion of the compound of formula I into the mixture of (3aα,5aβ,9aα,9bβ)-dodecahydro-3a,6,6-,9a-tetra-methylnaphthol[2,1-b]furan and (3aα,5aβ,-9aα,9bα)dodecahydro-3a,6,6,9a-tetramethylnaphthol[2,1-b]furan can be effected in manner known per se, for example by cyclizing the corresponding compound I or the mixture of the two compounds I (whereby the respective compound I itself is present as a pure isomer or as a mixture of isomers) to sclareolid and, optionally, further isomers such as, for example, episclareolid and isosclareolid, reducing the cyclization product to the corresponding diol (mixed) and finally dehydrating the diol product. A typical multistage process for the conversion of the compound(s) of formula I into the mixture of (3aα,5aβ,9aα,9bβ)-dodecahydro3a,6,6,9a-tetramethylnaphthol[2,1-b]furan and (3aα,-5aβ,9aα,9bα)-dodecahydro3a,6,6,9a-tetramethylnaphtho[2,1-b]furan is given in the following Reaction Scheme in which the notations " " and " " signify that the corresponding residue is situated above and, respectively, below the plane of the molecule.

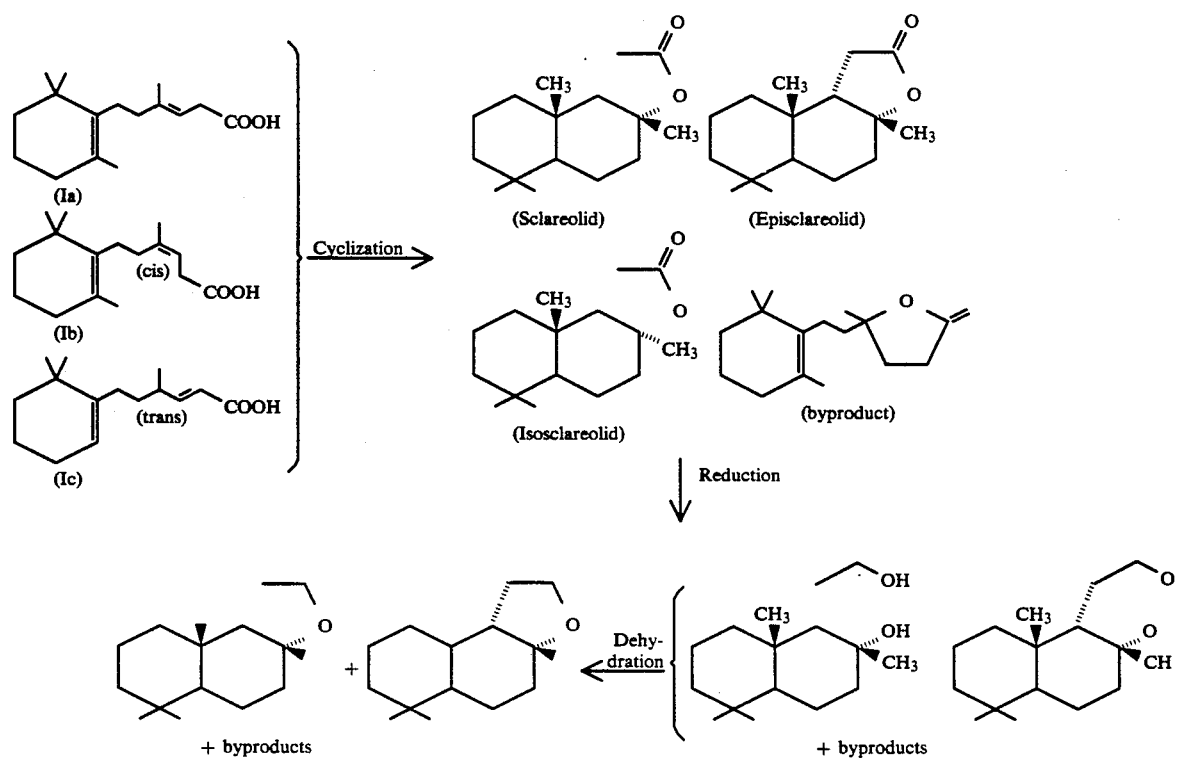

According to Lucius (Archiv der Pharmazie 291, 55 (1958); Chem. Ber. 1960, 2663; Angew. Chem. 68, 247 (1956); and DDR Patent 13535) the cyclization can be carried out using a mixture of formic acid and sulphuric acid, although the exact stereochemistry of the thus-obtained three lactones could not be characterized unequivocally. A Saito et al. (Chem. Lett. 1981, 757-760 and Chem. Lett. 1983, 729-732) have investigated the cyclization in detail and have assigned the exact stereochemistry to these lactones.

This cyclization comprises treating E-6-(2',6',6'-trimethyl-cyclohex-1'-en-1'-yl)4-methyl-hex-3-enoic acid (Ia) with tin tetrachloride in methylene chloride at −78° C., which gives a mixture of (±) sclareolid and (±) episclareolid in a weight ratio of about 8:1. Treatment of Z-6-(2',6',6'-trimethyl-cyclohex-1'-en-1'-yl)-4-methyl-hex-3-enoic acid (Ib) with tin tetrachloride in methylene chloride at −20° C. gives only episclareolid. The cyclization with tin tetrachloride was described first by A. Saito et al. (ibid.) (See also H. Kaneko et al., Japanese Patent Publication 123483A/1985). In place of tin tetrachloride, the cyclization can also be carried out with trifluoroacetic acid in methylene chloride at 0° C. (See European Patent Publication 165,458 and T. Kawanobe et al., Agr. Biol. Chem. 50(6), 1475 (1985)).

The reduction of the cyclization product (sclareolid and possibly other lactones) is conveniently effected, inter alia, using sodium bis(2-methoxyethoxy)aluminum dihydride (Redal) as the reducing agent (see European Patent Publication 165,458). Further reduction methods have become known, for example, from Maslo-Zhir Prom. st. 7, 29-30 (1980) (Chem. Abs. 94, 15913 q), Maslo-Zhir Prom. st. 12, 25-26 (1979) (Chem. Abs. 93, 114751 w) and USSR Patent 559,916 (Chem. Abs. 87, 136064 c).

The manufacture of the mixture of (3aα,5aβ,-9aα,9bβ)-dodecahydro-3a,6,6,9a-tetramethylnaphtho[2,1-b]furan and (3aα,5aβ,9aα,9bα)-dodecahydro-3a,6,6,9a-tetramethylnaphtho[2,1-b]furan from the diol (mixed by dehydration can be carried out using naphthalene-β-sulphonic acid, (see e.g. Stoll et al., Helv. Chim. Acta. 33, 1251 (1950), Swiss Patent 299,369 and U.S. Pat. No. 2,809,996), p-toluenesulphonic acid (USSR Patent 345.153, Byul. Izobret 22, 94 (1972), Chem. Abs. 78, 111554p and European Patent Publication 170.955), sulphuric acid (Austral. J. Chem 24, 583 (1971), Chem. Abs. 74, 76550c), aluminum oxide (See above references concerning naphthalene-β-sulphonic acid and Japanese Patent Publication 61.033184), toluenesulphonyl chloride (European Patent Publication 165,458, Austral. J. Chem. 24, 583 (1971) and Chem. Abs. 74, 76550c), phosphours oxychloride (German Offenlegungsschrift 3240054) and dimethyl sulphoxide/trimethylsilyl chloride (Synthesis 1983, 219) as a catalyst.

ILLUSTRATION OF THE PREFERRED EMBODIMENTS

The following Examples illustrate the invention in more detail.

Example 1

A. Preparation of 6-(2',6',6'-trimethyl-cyclohex-1'-en-1'-yl)-4-methyl-hex-2/3-enenitrile A solution of 100 g (0.48 mol) of 4-(2',6',6'-trimethyl-cyclohex-1'-en-1'-yl)-2-methyl-butanal in 130 ml of toluene is added rapidly at reflux temperature to a solution of 120 ml of pyridine, 6.4 ml of piperidine and 48 g (0.56 mol) of cyanoacetic acid in 260 ml of toluene. The mixture is stirred at reflux temperature for 6 hours while separating the water formed in the reaction and is subsequently stirred at room temperature for about 16 hours.

Then, the toluene is distilled off, water is added, the mixture is extracted with diethyl ether and the organic phase is washed in sequence with 2N hydrochloric acid, 2N sodium hydroxide solution and water, dried over anhydrous magnesium sulphate and evaporated to dryness under reduced pressure. In this manner there are obtained 100 g (90% of the theoretical yield) of a mixture of isomers which has a boiling point in the range of about 89° C. to about 126° C. and which consists of the following isomers according to gas chromatography:

(a) Z-6-(2',6',6'-Trimethyl-cyclohex-1'-en-1'-yl)-4-methylhex-2-enenitrile (2.5%);
(b) E-6-(2',6',6'-trimethyl-cyclohex-1'-en-1'-yl)-4-methylhex-2-enenitrile (2.2%);
(c) Z-6-(2',6',6'-trimethyl-cyclohex-1'-en-1'-yl)-4-methylhex-3-enenitrile (23%); and
(d) E-6-(2',6',6'-trimethyl-cyclohex-1'-en-1'-yl)-4-methylhex-3-enenitrile (70%).

Spectroscopic data:
Isomer (a):
$^1$H-NMR (CDCl$_3$; 400 MHz) 6.295 ppm [dd, J=10.8, J=10.8, H-C(3)], 5.295 ppm [d, J=10.8, H-C(2)], 1.56 ppm [s, CH$_3$-C(2')], 1.09 ppm [d, J=7, CH$_3$-C(4)], 1.06 ppm [s, (CH$_3$)$_2$-C(6')];

mass spectrum (m/e): 231(18), 216(98), 199(6,2), 188(5), 175(14), 160(13), 123(100), 107(28), 95(66), 81(71), 67(38), 55(38), 41(63).

Isomer (b):
$^1$H-NMR (CDCl$_3$; 400 MHz) 6.66 ppm [dd, J=8, J=17, H-C(3)], 5.315 ppm [dd, J=17, J=1, H-C(2)], 1.555 ppm [s, CH$_3$-C(2')], 1.08 ppm (d, J=7, CH$_3$-CH(4)], 0.975 ppm [s, (CH$_3$)$_2$-C(6')];

mass spectrum (m/e): 231(13), 216(40), 199(2), 188(3), 175(6,2), 160(5), 123(100), 107(16), 95(37), 81(51), 67(41), 55(34), 41(25).

Isomer (c):
Infrared spectrum 2250 cm$^{-1}$;
$^1$H-NMR (CDCl$_3$; 400 MHz) 5.14 ppm [ddd, J=7, J=7, J=1.4, H-C(3)], 3.065 ppm, [dd, J=7, J=1,4, H$_2$-C(2)], 2.06 ppm [s broad, H$_2$-C(5)-C(6)-H$_2$], 1.925 ppm (dd broad, J=7, J=7, H$_2$-C(3')], 1.805 ppm [d, J=1,4, CH$_3$-C(4)], 1.645 ppm [s, CH$_3$-C(2')], 1.015 ppm [s, (CH$_3$)$_2$-C(6')];

mass spectrum (m/e) 231(3), 216(3), 175(3), 137(100), 121(7), 109(10), 95(78), 81(77), 67(22), 57(18), 41(27).

Isomer (d):
Infrared spectrum 2250 cm$^{-1}$;
$^1$H-NMR (CDCl$_3$; 400 MHz) 5.195 ppm [dd, J=7, J=7, H-C(3)], 3.05 ppm [d, J=7, H$_2$-C(2)], 2.07 ppm [s, H$_2$-C(5)-C(6)-H$_2$], 1.91 ppm [dd broad, J=7, J=7, H$_2$-C(3')], 1.715 ppm [d, J=0.8, CH$_3$-C(4)], 1.595 ppm [s, CH$_3$-C(2')], 0.99 ppm [s, (CH$_3$)$_2$-C(6')];

mass spectrum (m/e) 231(4), 216(2), 175(3), 137(100), 121(9), 109(9,5), 95(64), 81(56), 67(14), 57(11), 41(17).

B. Manufacture of 6-(2',6',6'-trimethyl-cyclohex-1'-en-1'-yl)-4-methyl-hex-2/3-enoic acid 300 g of a mixture containing 23 weight percent of Z-6-(2',6',6'-trimethyl-cyclohex-1'-en-1'-yl)-4-methyl-hex-3-enenitrile and 70 weight percent of the corresponding E-isomer (prepared according to part A) are dissolved in an aqueous potassium hydroxide solution [182.3 g (3.25M) KOH+220 ml H$_2$O] and added dropwise at room temperature to 1.6l of ethanol. The reaction mixture is then heated at reflux temperature for 6 hours while stirring. The ethanol is subsequently distilled off and the residue is taken up in diethyl ether. Water is added to the ether solution and the mixture is treated dropwise with 2N hydro- chloric acid while stirring and cooling. The separated aqueous phase is extracted with diethyl ether, the combined organic phases are washed neutral with water, dried over anhydrous magnesium sulphate and evaporated to dryness under reduced pressure. In this manner there are obtained 315 g of a mixture of isomers which consists of the following isomers according to gas chromatography:

(e) E-6-(2',6',6'-Trimethyl-cyclohex-1'-en-1'-yl)-4-methylhex-2-enoic acid (3%);
(f) Z-6-(2',6',6'-trimethyl-cyclohex-1'-en-1'-yl)-4-methylhex-3-enoic acid (29%); and
(g) E-6-(2',6',6'-trimethyl-cyclohex-1'-en-1'-yl)-4-methylhex-3-enoic acid (61%).

Example 2

A. Preparation of ethyl 6-(2',6',6'-trimethyl-cyclohex-1'-en-1'-yl)-4-methyl-2-cyano-hex-2-enoate 50 g (0.24 mol) of 4-(2',6',6'-trimethyl-cyclohex-1'-en-1'-yl)-2-methyl-butanal are dissolved in 125 ml of ethanol and 3.5 g of potassium fluoride are added thereto. 27.2 g (240 mmol) of ethyl cyanoacetate are then added dropwise thereto and a slight warming of the reaction mixture is observed. The mixture is then stirred at room temperature for 1 hour and subsequently concentrated, and the solid material is filtered off. After distillation of the residue under a high vacuum (15·10$^{-4}$ mbar) there are obtained 55 g of ethyl 6-(2',6',6'-trimethylcyclohex-1'-en-1'-yl)-4-methyl-2-cyano-hex-2-enoate, b.p. 152° C./5·10$^{-4}$ Torr; infrared spectrum: 2230, 1735, 1625, 1260 cm$^{-1}$; $^1$H-NMR (CDCl$_3$; 200 MHz): 7.48 ppm [d, J=10.5, C(3)-H], 4.32 ppm (ddd, J=7, CH$_3$-CH$_2$-O), 2.86 ppm [m, C(4)-H], 1.56 ppm (s, C(2')-CH$_3$), 1.36 ppm (dd, J=7, CH$_3$-CH$_2$-O), 1.16 ppm [d, J=6.5, CH$_3$-CH(4)], 0.96 ppm [s, (CH$_3$)$_2$C(6')]; $^{13}$C-NMR (CDCl$_3$; MHz): 168.0 ppm (d), 161.19 ppm (s), 136.3 (s), 127.4 ppm (s), 113.5 ppm (s), 108.4 ppm (s), 62.2 ppm (t), 39.6 ppm (t), 37.7 ppm (d), 36.3 ppm (t), 34.7 ppm (s), 32.5 ppm (t), 28.4 ppm (q), 26.2 ppm (t), 19.7 ppm (q), 19.3 ppm (t), 18.9 ppm (q), 13.9 ppm (q); mass spectrum (m/e): 303(19), 288(60), 260(7), 242(40), 230(3,4), 214(9), 175(10), 137(19), 123(100), 107(21), 95(54), 81(38), 67(21), 55(26,5), 41(37), 28(44).

B. Manufacture of 6-(2',6',6'-trimethyl-cyclohex-1'-en-1'-yl)-4-methyl-hex-2/3-enoic acid A solution of 7 g of ethyl 6-(2',6',6'-trimethyl-cyclohex-1'-en-1'-yl)-4-methyl-2-cyano-hex-2-enoate in 20 ml of ethylene glycol is treated with 5.2 g of potassium hydroxide in 5.2 ml of water. The reaction mixture is then heated at 130° C. (internal temperature 115° C.) for 22.5 hours while stirring. The separated aqueous phase is extracted with diethyl ether and adjusted to pH 7 by the addition of 10 percent hydrochloric acid. After further extraction of the aqueous phase with diethyl ether the organic phase is dried over anhydrous magnesium sulphate and evaporated to dryness under reduced pressure. In this manner there are obtained 3.39 g (58% of the theoretical yield) of a mixture of isomers which consists of the following isomers according to gas chromatography:

(a) E-6-(2',6',6'-Trimethyl-cyclohex-1'-en-1'-yl)-4-methyl-hex-2-enoic acid (21%);

(b) Z-6-(2',6',6'-Trimethyl-cyclohex-1'-en-1'-yl)-4-methyl-hex-3-enoic acid (18%); and
(c) E-6-(2',6',6'-Trimethyl-cyclohex-1'-en-1'-yl)-4-methyl-hex-3-enoic acid (45%).

Example 3

Preparation of methyl 6-(2',6',6'-trimethyl-cyclohex-1'-en-1'-yl)-4-methyl-2-cyano-hex-2-enoate 50 g (0.24 mol) of 4-(2',6',6'-trimethyl-cyclohex-1'-en-1'-yl)-2-methyl-butanal are dissolved in 125 ml of ethanol and 3.5 g of potassium fluoride are added thereto. 23.8 g (0.24 mol) of methyl cyanoacetate are then added dropwise thereto at 15° C. within 15 minutes and the reaction mixture is stirred at room temperature for 1.5 hours. The mixture is subsequently concentrated and the solid material is filtered off. After distillation of the residue (69.7 g) under a high vacuum ($2 \times 10^{-5}$ mbar) in a bulb-tube there are obtained 49.3 g of methyl 6-(2',6',6'-trimethylcyclohex-1'-en-1'-yl)-4-methyl-2-cyano-hex-2-enoate, b.p. 178° C./$10^{-4}$ mbar; infrared spectrum (liquid): 2230, 1740, 1625 cm$^{-1}$; $^1$H-NMR (CDCl$_3$, 200 MHz): 7.5 ppm [d, J=11, C(3)-H]; 3.88 ppm (s, CO$_2$CH$_3$), 2.86 ppm [m, C(4)], 1.56 ppm [s, CH$_3$-C(2')], 1.16 ppm [d, J=6,8, CH$_3$-C(4)], 0.96 ppm [s, (CH$_3$)$_2$-C(6')]; mass spectrum (m/e): 289(17), 274(60), 242(38), 214(14), 197(5), 175(7,7), 152(7), 137(21), 123(100), 107(28), 95(66), 81(65), 67(42), 55(31), 41(47), 29(21.8).

Example 4

Preparation of isopropyl 6(2',6',6'-trimethyl-cyclohex-1'-en-1'-yl)-4-methyl-2-cyano-hex-2-enoate The title compound is produced analogously to the procedure described in Example 3 from 4-(2',6',6'-trimethylcyclohex-1'-en-1'-yl)-2-methyl-butanal and isopropyl cyanoacetate.

Physical data:
B.p. 115° C./$2 \cdot 10^{-5}$ mbar;
infrared spectrum (liquid): 2230, 1735, 1625 cm$^{-1}$;
$^1$H-NMR (CDCl$_3$, 200 MHz): 7.46 ppm [d, J=11, C(3)-H], 5.14 ppm [m, J=6,4, CH(CH$_3$)$_2$], 2.85 ppm [m, C(4)-H], 1.56 ppm [s, CH$_3$-C(2')], 1.34 ppm (d, J=6,4, CH$_3$CHCH$_3$), 1.33 ppm [d, J=6,4, CH$_3$CHCH$_3$], 1.16 ppm [d, J=6.8, CH$_3$-C(4)], 0.98 ppm [s, (CH$_3$)$_2$-C(6')]; mass spectrum (m/e): 317(15), 302(32), 275(10), 260(56), 242(40), 214(10), 201(4,2), 191(8), 178(13), 137(32), 123(100), 107(25), 95(56), 81(60), 69(29), 55(28), 43(50), 28(47).

Example 5

Preparation of n-butyl 6-(2',6',6'-trimethyl-cyclohex-1'-en-1'-yl)-4-methyl-2-cyano-hex-2-enoate The title compound is produced analogously to the procedure described in Example 3 from 4-(2',6',6-trimethylcyclohex-1'-en-1'-yl)-2-methyl-butanal and n-butyl cyanoacetate.

Physical data
B.p. 120° C./$2 \cdot 20^{-5}$ mbar;
infrared spectrum (liquid): 2230, 1730, 1625 cm$^{-1}$;
$^1$H-NMR (CDCl$_3$, 200 MHz): 7.47 ppm (d, J=10.5, C(3)-H), 4.26 ppm (ddd, J=6,6, J=6,6, J=1, -O-CH$_2$), 2.86 ppm [m, C(4)-H], 1.56 ppm [s, CH$_3$-C(2')], 1.16 ppm [d, J=7, CH$_3$-C(4)], 0.96 ppm [s, (CH$_3$)$_2$-C(6')]; mass spectrum (m/e): 331(13), 316(42), 288(28), 274(4), 267(11), 260(17), 242(45), 214(14), 175(14), 137(25), 123(100), 107(29), 95(65), 81(65), 69(33), 55(45), 41(62), 28(31).

Example 6

Preparation of tert,butyl 6-(2',6',6'-trimethyl-cyclohex-1'-en-1'-yl)-4-methyl-2-cyano-hex-2-enoate The title compound is produced analogously to the procedure described in Example 3 from 4-(2',6',6'-trimethylcyclohex-1'-en-1'-yl)-2-methyl-butanal and tert.butyl cyanoacetate.

Physical data:
B.p. 120° C./$2 \cdot 10^{-5}$ mbar;
infrared spectrum (liquid): 2230, 1735, 1625 cm$^{-1}$;
$^1$H-NMR (CDCl$_3$, 200 MHz): 7.38 ppm [d, J=11, C(3)-H], 2.83 ppm [m, C(4)-H], 1.55 ppm [s, C(CH$_3$)$_2$], 1.15 ppm [dd, J=6.5, CH$_3$-CH(4)], 0.97 ppm [s, (CH$_3$)$_2$C(6')];
mass spectrum (m/e): 331(2), 275(24), 274(41), 260(40), 242(12), 231(4), 216(7), 194(10), 175(8), 137(27), 123(51), 107(18), 95(42), 81(50), 69(24), 87(85), 41(100), 28(60).

We claim:

1. A process for the manufacture of a mixture of (3aα,5aβ,9aα,9bβ)-dodecahydro-3a,6,6,9a-tetramethyl-naptho-[2,1-b]furan and (3aα,5aβ,9aα,9bα)-dodecahydro-3a,6,6,9a-tetramethylnaphthol[2,1-b]furan which comprises:
(a) saponifying a compound of the formula II

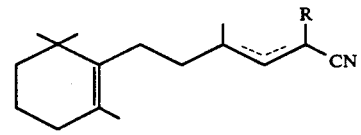

wherein
one of the bonds - - - denotes a single bond and the other denotes a double bond, and, R represents hydrogen or the ester group COOR$^1$, in which R$^1$ represents a lower alkyl or aryl group, and,
where R in formula II represents the ester group COOR$^1$, decarboxylating said group,
in a solvent selected from the group consisting of inert protic organic solvents, aromatic hydrocarbons, cyclic ethers and water, with a base, at temperatures between about 20° C. and about 130° C., to produce a compound of the formula I

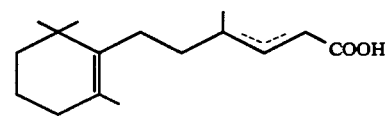

and,
(b) converting said compound of formula I to said mixture.

2. A process according to claim 1, wherein said solvent is an alcohol, a glycol, benzene, toluene, xylene, tetrahydrofuran dioxan or water; said base is an alkali metal hydroxide and said temperature is the reflux temperature of the reaction mixture.

3. A process according to claim 2 or 3, wherein said compound of formula II is prepared by reacting 4-

(2',6',6'-trimethyl-cyclohex-1'-en-1'-yl)-2-methyl-butanal with a compound of the formula IV

NCCH₂COOR²         IV wherein R² represents hydrogen, a lower alkyl group or an aryl group, in the presence of (a) an organic solvent selected from the group consisting of aromatic hydrocarbons, alcohols, aliphatic ethers and aromatic ethers, and, b) a weak base or a Lewis acid, at a temperature of from room temperature to about 180° C.

4. A compound of the formula

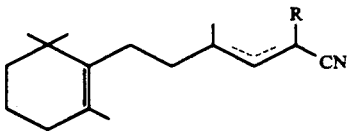     II wherein one of the bonds denotes a single bond and the other denotes a double bond and R represents hydrogen or the ester group —COOR¹ in which R¹ represents a lower alkyl or aryl group.

5. A compound according to claim 4, selected from the group consisting of 6-(2',6',6'-Trimethyl-cyclohex-1'-en-1'-yl)-4-methyl-hex-3-enenitrile; methyl 6-(2',6',6'-trimethyl-cyclohex-1'-en-1'-yl)-4-methyl-2-cyano-hex-2-enoate; ethyl 6-(2',6',6'-trimethyl-cyclohex-1'-en-1'-yl)-4-methyl-2-cyano-hex-2-enoate; isopropyl 6-(2',6',6'-trimethyl-cyclohex-1'-en-1'-yl)-4-methyl-2-cyano-hex-2-enoate: n-butyl 6-(2',6',6'-trimethyl-cyclohex-1'-en-1'-yl)-4-methyl-2-cyanohex-2-enoate; and, tert.butyl 6-(2',6',6'-trimethyl-cyclohex-1'-en-1'-yl)-4-methyl-2-cyano-hex-2-enoate.

* * * * *

UNITED STATES PATENT AND TRADEMARK OFFICE
CERTIFICATE OF CORRECTION

PATENT NO. : 5,292,902

DATED : March 8, 1994

INVENTOR(S) : Daniel Helmlinger

It is certified that error appears in the above-identified patent and that said Letters Patent is hereby corrected as shown below:

In the Title Page, [57], Abstract: fourth line from bottom, after the word "bonds" and before the word "denotes" insert

-- ...... --

In Column 2, line 10, after the word "bonds" and before the word "denotes" insert

-- ...... --

In claim 1, Column 10, line 41, after the word "bonds" and before the word "denotes" delete "...." and insert therefor

-- ...... --

UNITED STATES PATENT AND TRADEMARK OFFICE
CERTIFICATE OF CORRECTION

PATENT NO. : 5,292,902   Page 2 of 2
DATED     : March 8, 1994
INVENTOR(S): Daniel Helmlinger It is certified that error appears in the above-indentified patent and that said Letters Patent is hereby corrected as shown below:

In claim 4, Column 12, line 9, after the word "bonds" and before the word "denotes" insert -- ...... --

Signed and Sealed this

Twenty-sixth Day of July, 1994

Attest:

BRUCE LEHMAN

Attesting Officer    Commissioner of Patents and Trademarks